US006887428B2

United States Patent
Wernz et al.

(10) Patent No.: US 6,887,428 B2
(45) Date of Patent: May 3, 2005

(54) APPARATUS FOR TREATING CYTOLOGICAL OR HISTOLOGICAL SPECIMENS

(75) Inventors: Martin Wernz, Heidelberg (DE); Stefan Thiem, Heidelberg (DE); Eric Barth, Leimen (DE)

(73) Assignee: Leica Microsystems Nussloch GmbH, Nussloch (DE)

(*) Notice: Subject to any disclaimer, the term of this patent is extended or adjusted under 35 U.S.C. 154(b) by 372 days.

(21) Appl. No.: 09/932,889

(22) Filed: Aug. 20, 2001

(65) Prior Publication Data

US 2002/0076351 A1 Jun. 20, 2002

(30) Foreign Application Priority Data

Aug. 22, 2000 (DE) .......................................... 100 41 231

(51) Int. Cl.⁷ ............................................... G01N 35/02
(52) U.S. Cl. ......................................... 422/63; 422/301
(58) Field of Search ...................... 422/63–67, 300–304; 901/1–9, 14–29

(56) References Cited

U.S. PATENT DOCUMENTS

| 4,830,565 A | * | 5/1989 | Bucher et al. .......... 414/416.01 |
| 5,046,880 A | * | 9/1991 | Steinhilber ............... 403/109.5 |
| 5,417,123 A |   | 5/1995 | D'Autry ................... 73/864.25 |
| 5,895,628 A |   | 4/1999 | Heid et al. ...................... 422/65 |
| 5,948,359 A |   | 9/1999 | Kalra et al. .................... 422/65 |
| 6,080,363 A |   | 6/2000 | Takahashi et al. ............ 422/65 |
| 6,293,750 B1 | * | 9/2001 | Cohen et al. ............. 414/744.4 |

FOREIGN PATENT DOCUMENTS

| FR | 2617077 A1 | * 12/1988 | ........... B23P/19/00 |
| GB | 2196428 |   4/1988 | .......... G01N/35/06 |
| SU | 1191256 A | * 11/1985 | ............ B23Q/7/04 |

* cited by examiner

Primary Examiner—Yelena G. Gakh
(74) Attorney, Agent, or Firm—Hodgson Russ LLP

(57) ABSTRACT

An apparatus for treating objects, in particular cytological or histological specimens, having multiple processing stations (2) and a transport device (4) for delivering the objects into and out of the processing stations (2), is characterized in that the transport device (4) comprises a robot arm (5) that is movable in three dimensions and provides for arbitrary positioning of the objects.

3 Claims, 7 Drawing Sheets

APPARATUS FOR TREATING CYTOLOGICAL OR HISTOLOGICAL SPECIMENS

CROSS REFERENCE TO RELATED APPLICATIONS

This invention claims priority of the German patent application 100 41 231.9 filed Aug. 22, 2000 which is incorporated by reference herein.

FIELD OF THE INVENTION

The invention concerns an apparatus for treating objects, in particular cytological or histological specimens, having multiple processing stations and a transport device for delivering the objects into and out of the processing stations.

BACKGROUND OF THE INVENTION

Apparatuses of the generic type are known from a wide variety of fields. Very generally, they are apparatuses used for handling and/or processing objects of any kind. The objects are delivered either to a single processing station or to multiple processing stations, usually in a predefined sequence; processed therein; and then lastly transported away from the processing station, in which context different groups of processing stations can be arranged behind and/or next to another.

The reader is referred, purely by way of example, to EP 0 849 582 A2. This document discloses an apparatus for treating objects, in particular cytological or histological specimens. In this, cytological or histological specimens are delivered by way of an object carrier or basket (often also called a "rack" in technical terminology) to an automatic stainer, the automatic stainer comprising multiple processing stations.

In the field of cytology and histology, transport of the samples to be treated was hitherto accomplished using motion mechanisms that are constructed on the X-Y-Z principle using three linear axes, or using a vertical linear axis with additional rotational motion. If a total of three linear axes are provided, samples can be picked up from a rectangularly arranged field and set down into it. The size of this field is determined by the X and Y linear axes. If transport is performed on the basis of only one vertical linear axis with additional rotational motion, then the sample can be picked up and set down along a circular path.

The aforementioned motion mechanisms are problematic in practical use, however, in that the samples to be positioned and/or picked up cannot be moved unrestrictedly. The use of corresponding motion mechanisms is thus greatly limited, or the use of such motion mechanisms requires a very particular (and rigid) arrangement of the processing stations.

SUMMARY OF THE INVENTION

It is thus the object of the present invention to configure and further develop an apparatus for treating objects, in particular cytological or histological specimens, so as to yield the greatest possible variability in terms of the arrangement of the processing stations and in terms of the utilization of the transport device.

The aforesaid object is achieved by way of the features of the present invention. According to the invention, a generic apparatus for treating objects, in particular cytological or histological specimens, is characterized in that the transport device comprises a robot arm that is movable in three dimensions and provides for arbitrary positioning of the objects.

What has been recognized according to the present invention is that a greater variability of the apparatus can be achieved by deviating from the proven motion mechanisms (X-Y-Z principle or vertical linear axis with additional rotational motion). It has also been recognized that the hitherto successful motion mechanisms can be replaced by a very particular transport device which comprises a robot arm that is movable in three dimensions and provides for arbitrary positioning of the objects. This ensures that any conceivable position can be reached, so that objects are positionable in the context of any arbitrary arrangement of the processing stations, specifically in accordance with definable positions in both two and three dimensions.

For concrete receiving of the objects or of an object holder or rack, the robot arm could comprise at its free end at least one gripper, so that handling of the objects with the aid of the gripper is possible. Advantageously, the gripper is arranged rotatably on the robot arm, so that any desired rotation of the objects, and thus more extensive positioning, is possible.

In additionally advantageous fashion, the gripper can be lowered toward the processing station; lowering of the gripper can be accomplished directly at its articulation, or indirectly via the robot arm. The gripper could moreover be actuable via the robot arm both in its rotary motion and/or lowering and in its actual (gripping) activity. A separate drive provided for that purpose could be associated with the robot arm or also directly with the gripper.

For height adjustment of the robot arm but also for implementation of a rotary motion, the latter is arranged rotatably on a preferably vertically oriented longitudinal shaft, said longitudinal shaft being positioned and mounted at a suitable point inside the apparatus, preferably on its baseplate or on its housing. Concretely, the robot arm could be arranged rotatably at the upper end of the linear shaft, it being entirely conceivable that the robot arm is vertically displaceable along the linear shaft. A height adjustment of the robot arm could also, however, be implemented by the fact that the linear shaft as such—together with the robot arm—is height-adjustable in telescoping fashion or in a manner known per se.

Let it be noted at this juncture that the gripper can be articulated rotatably on the robot arm. In such a case the linear shaft could be height-adjustable together with the gripper, the aforementioned telescoping height adjustment of the linear shaft being achievable in very particularly advantageous fashion. It is also conceivable for an upper part of the linear shaft to slide in a lower receptacle or to be shiftable in its position therein.

It is furthermore conceivable for the linear shaft to be shiftable or movable in its position inside the baseplate or inside the housing of the apparatus. For that purpose, the linear shaft could be displaceable, preferably between the processing stations, along a rail or in the manner of an X-Y coordinate stage. A stationary configuration of the linear shaft is also conceivable, and is particularly simple in terms of design and therefore advantageous.

Concretely, the robot arm could comprise two partial arms joined pivotably to one another, so that assuming a rotary motion at the linear shaft and assuming a pivotable configuration of both partial arms, all desired positions are reachable. Assuming the height adjustment of the gripper already mentioned earlier, the latter can be positioned at any desired point in three dimensions, thus achieving a maximum degree of flexibility.

The partial arms of the robot arms, and optionally the gripper, could be rotationally driven via drive belts, the rotational drive being associated with the respective partial arm or with the partial arm that is rotatably associated with the linear shaft. For example, it is conceivable for the partial arm articulated on the linear shaft to have associated with it single common drive for rotating or pivoting the two partial arms, and optionally for rotating and/or actuating the gripper. Alternatively, it is possible for the partial arm articulated on the linear shaft to have associated with it preferably two independent drives for rotating or pivoting the two partial arms and optionally for rotating and/or actuating the gripper. This, too, contributes to the flexibility of the apparatus as a whole.

The gripper serving to receive the object or an object holder comprises, in additionally advantageous fashion, very particular receiving means for receiving the object or object holder. If the objects are always to be handled with an object holder, the receiving means could be designed in such a way that the gripper engages beneath the object holder, clamps it, or otherwise receives it into or onto itself. In very particularly advantageous fashion, the receiving means are configured in such a way that the gripper can be moved or placed onto the object holder from above, in that context receiving the object holder. For that purpose, the receiving means could comprise snap-lock means and/or closure means or locking means, reception and locking being accomplished by placing the gripper onto the object holder. Relevant detailed features of an exemplary embodiment are evident from the description of the Figures.

To increase throughput, the robot arm could comprise at its free end two identical grippers for concurrent reception of two object holders. The two grippers could have a common drive associated with them, so that the two respective object holders are handled simultaneously. It is also conceivable, however, for the grippers to comprise two mutually independent drives, so that independent or separate actuation of the grippers is possible.

Let it be noted furthermore that the apparatus according to the present invention can concretely be an automatic stainer, the processing stations each comprising a vessel for receiving liquids and for immersion of the objects or of the object holders carrying the object.

BRIEF DESCRIPTION OF THE DRAWINGS

There are various ways of advantageously embodying and developing the teaching of the present invention. The reader is referred, for that purpose, on the one hand to the claims subordinate to claim 1, and on the other hand to the explanation below of exemplary embodiments of the invention with reference to the drawings. In conjunction with the explanation of the preferred exemplary embodiments of the invention with reference to the drawings, an explanation is also given of generally preferred embodiments and developments of the teaching. In the drawings:

DETAILED DESCRIPTION OF THE INVENTION

Figure 1:
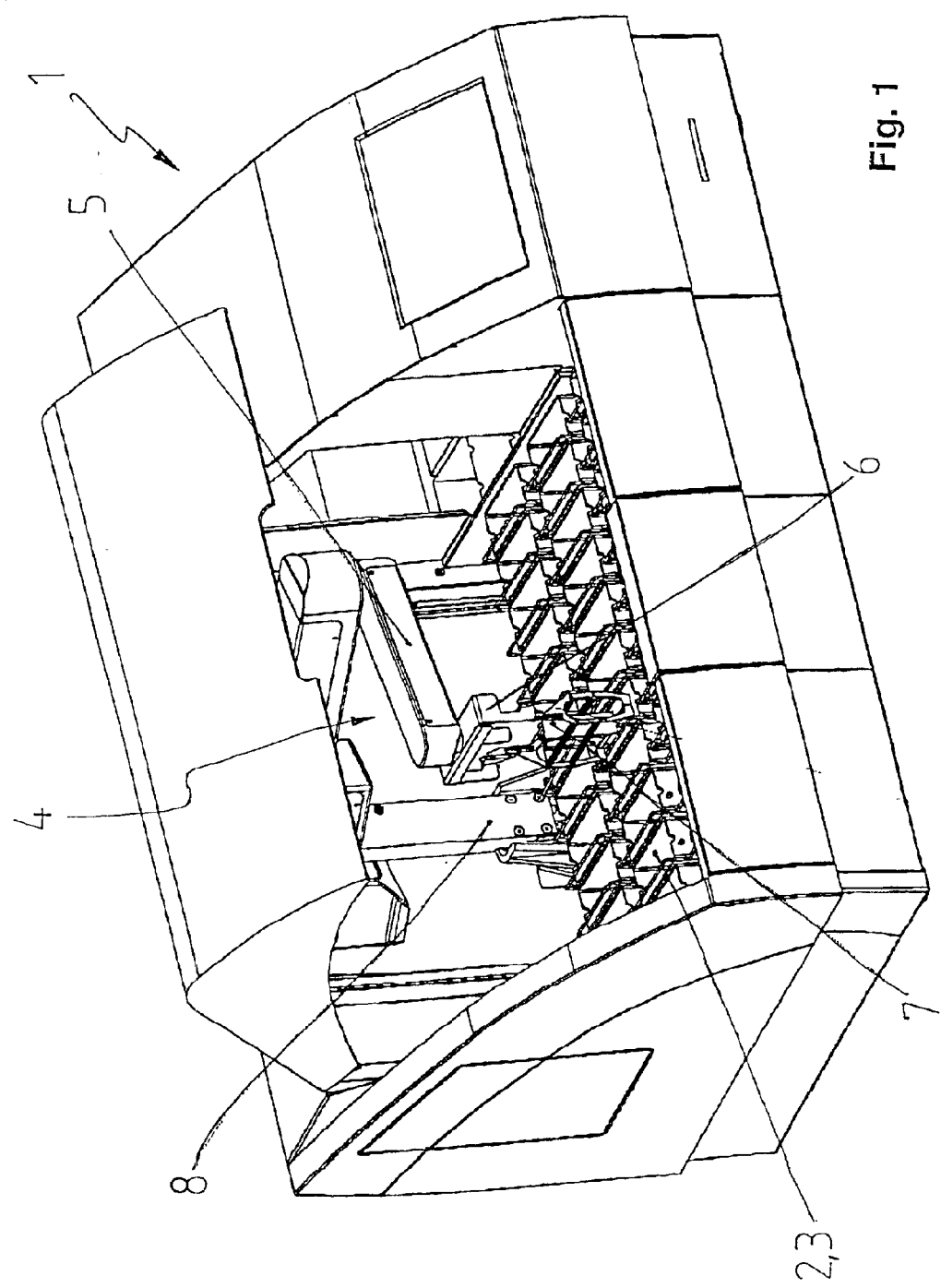
FIG. 1 schematically depicts the general construction of an apparatus according to the present invention, using the example of an automatic stainer according to the present invention.

FIG. 1 shows, in a schematic view, an exemplary embodiment of an apparatus according to the present invention for treating cytological or histological specimens, this being concretely an automatic stainer 1. Regarding the basic construction of an automatic stainer, the reader is referred to EP 0 849 582 A2.

Automatic stainer 1 comprises multiple processing stations 2, these being defined here by vessels 3 for liquids or reagents.

Also provided is a transport device 4 which moves objects (not shown in the Figures) into and out of processing stations 2.

According to the present invention, transport device 4 comprises a robot arm 5 that is movable in three dimensions and provides for arbitrary positioning of the objects. Said robot arm 5 ensures the greatest possible flexibility for transport device 4, specifically in that arbitrary positioning of the objects in three dimensions (i.e., concretely, inside the apparatus) is possible.

Also evident from FIG. 1 is the fact that robot arm 5 comprises at its free end a gripper 6 for receiving the objects or an object holder 7. The objects are delivered into vessel 3 together with object holder 7, and also moved out of vessel 3 again together with object holder 7.

Figure 2:
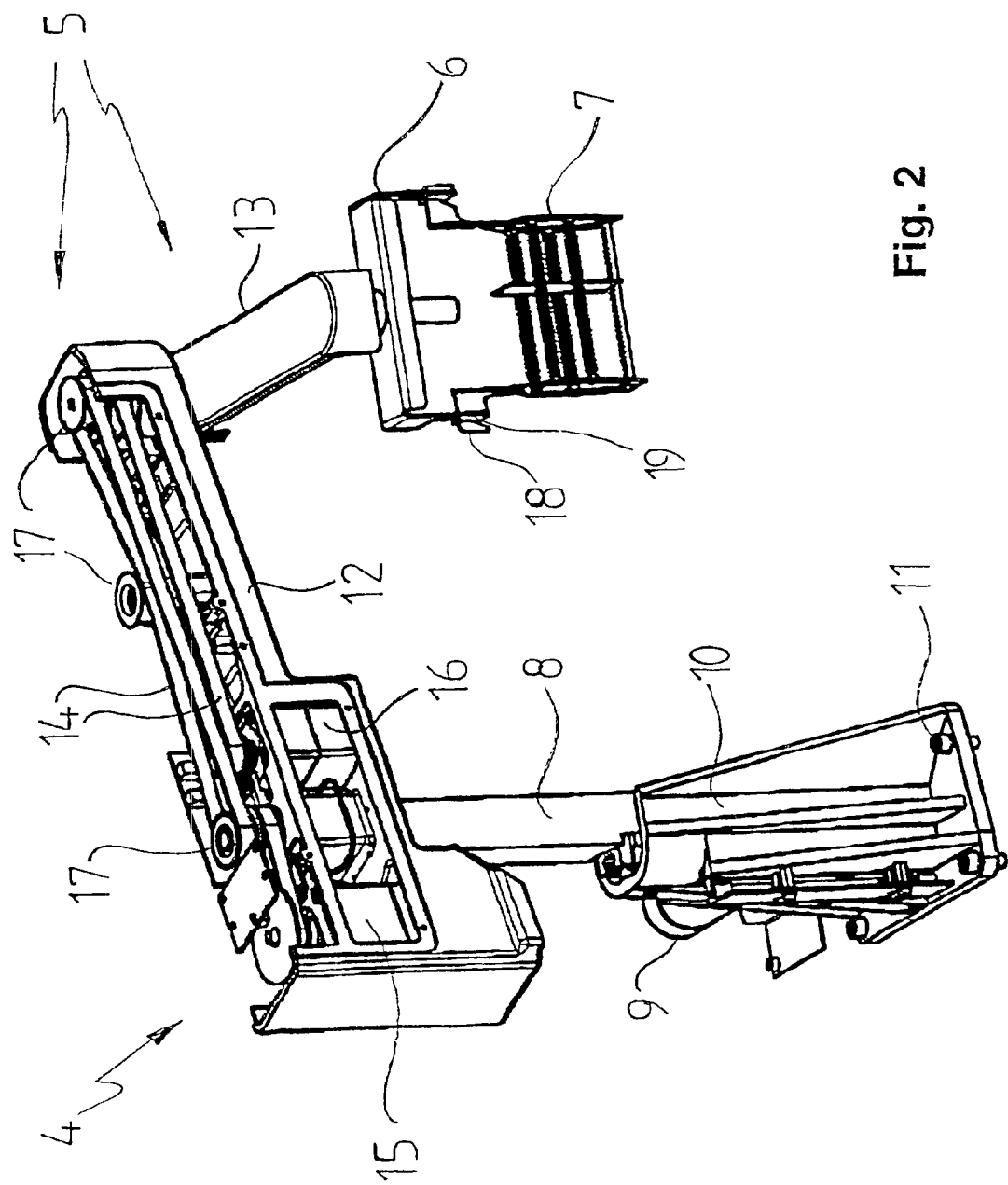
FIG. 2 schematically depicts the robot arm of the apparatus of FIG. 1.
Figure 3:
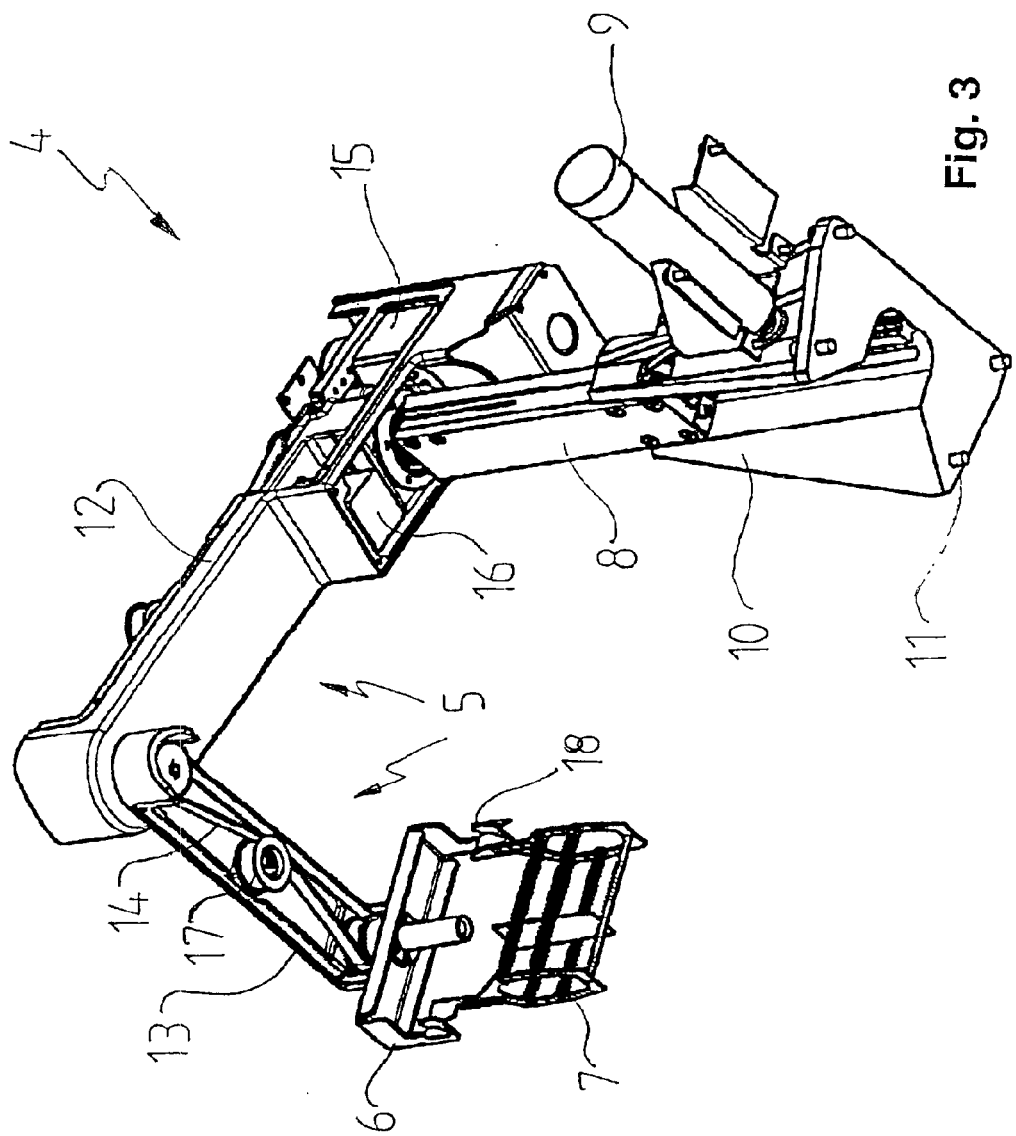
FIG. 3 schematically depicts the subject matter of FIG. 1 in a different view and angular position.

FIGS. 1, 2, and 3 together show that gripper 6 is rotatably arranged. Gripper 6 could be lowerable in the region of its articulation point, although such is not the case in the exemplary embodiment shown here.

FIGS. 1 through 3 moreover show clearly that robot arm 5 is arranged rotatably on a vertically oriented linear shaft 8. Concretely, robot arm 5 is arranged rotatably at the upper end of linear shaft 8, and linear shaft 8 can be adjusted as to its height. A separate drive 9 for height adjustment of linear shaft 8 is provided for that purpose, linear shaft 8 running in a guide 10. A telescoping configuration of linear shaft 8 is also conceivable.

FIGS. 2 and 3 show particularly clearly that in the exemplary embodiment selected here, linear shaft 8 is height-adjustable together with gripper 6. Because of the particular configuration of guide 10 and mounting means 11 provided there, it is apparent that in the exemplary embodiment selected here, linear shaft 8 is stationary. A movement capability of linear shaft 8 (between vessels 3) is possible.

It is further evident from FIGS. 1 through 3 that robot arm 5 comprises first and second partial arms 12, 13 joined pivotably to one another. FIGS. 2 and 3 show the partial arms without coverings in each case, so that the manner of operation of partial arms 12, 13 is easily visible. Concretely, partial arms 12, 13 and gripper 6 are rotationally driven via drive belts 14, partial arm 12 articulated on linear shaft 8 having associated with it independent drives 15, 16 for rotating or pivoting the two partial arms 12, 13 and for rotating gripper 6. The rotary motion is effected, from drives 15, 16, via drive belts 14 and via corresponding pulleys 17 that either divert the rotary motion to further drive belts 14 or pass on the rotary motion directly to the next respective component. Drive belts 14 can be, for example, toothed belts or conventional V-belts.

Figure 4:
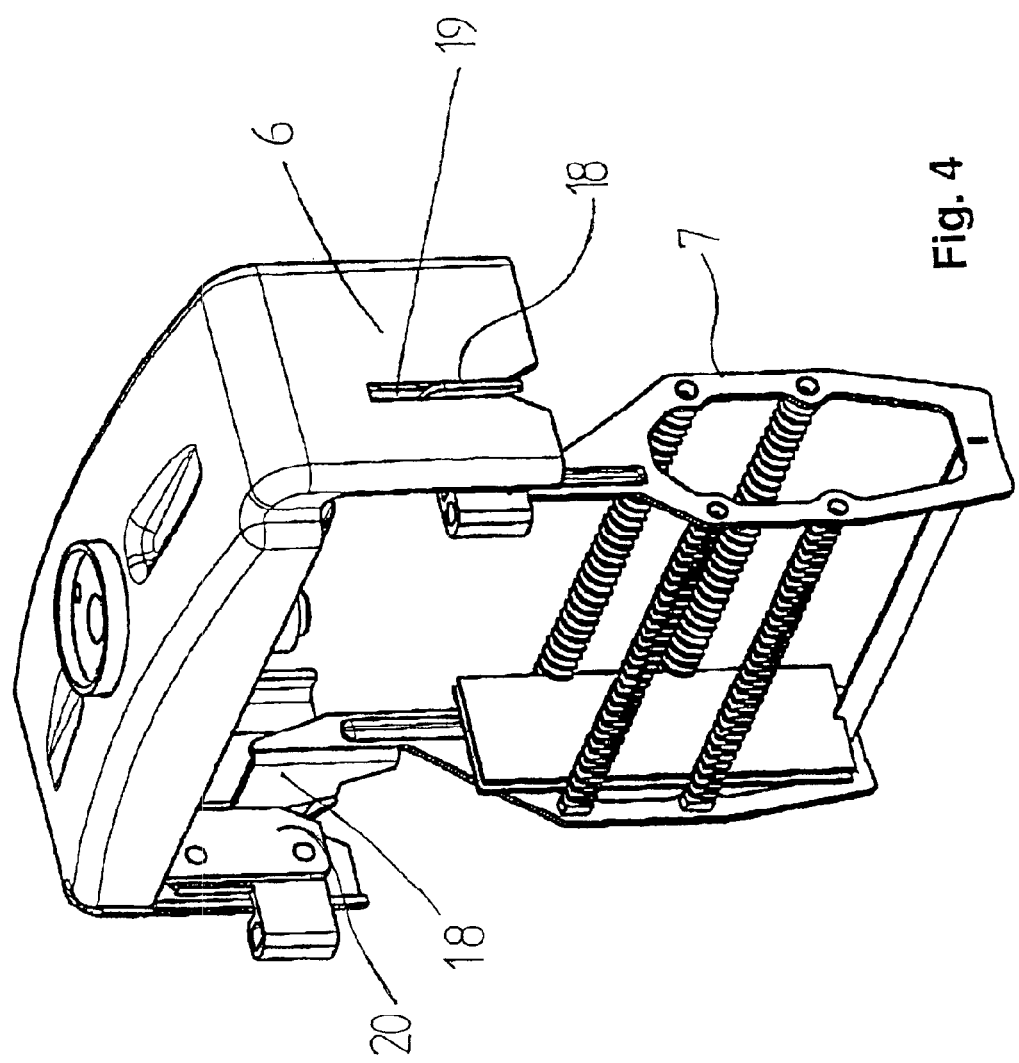
FIG. 4 schematically depicts a first exemplary embodiment of a gripper arranged at the free end of a robot arm.

FIGS. 2, 3, and 4 show a simple exemplary embodiment of a gripper 6 with object holder 7, in which hooks 18 of object holder 7 serving for reception engage into corresponding slots 19 of gripper 6 and are retained there. It is possible in this context for gripper 6 to travel onto object holder 7 from directly above and thereby to receive object holder 7.

Figure 5:
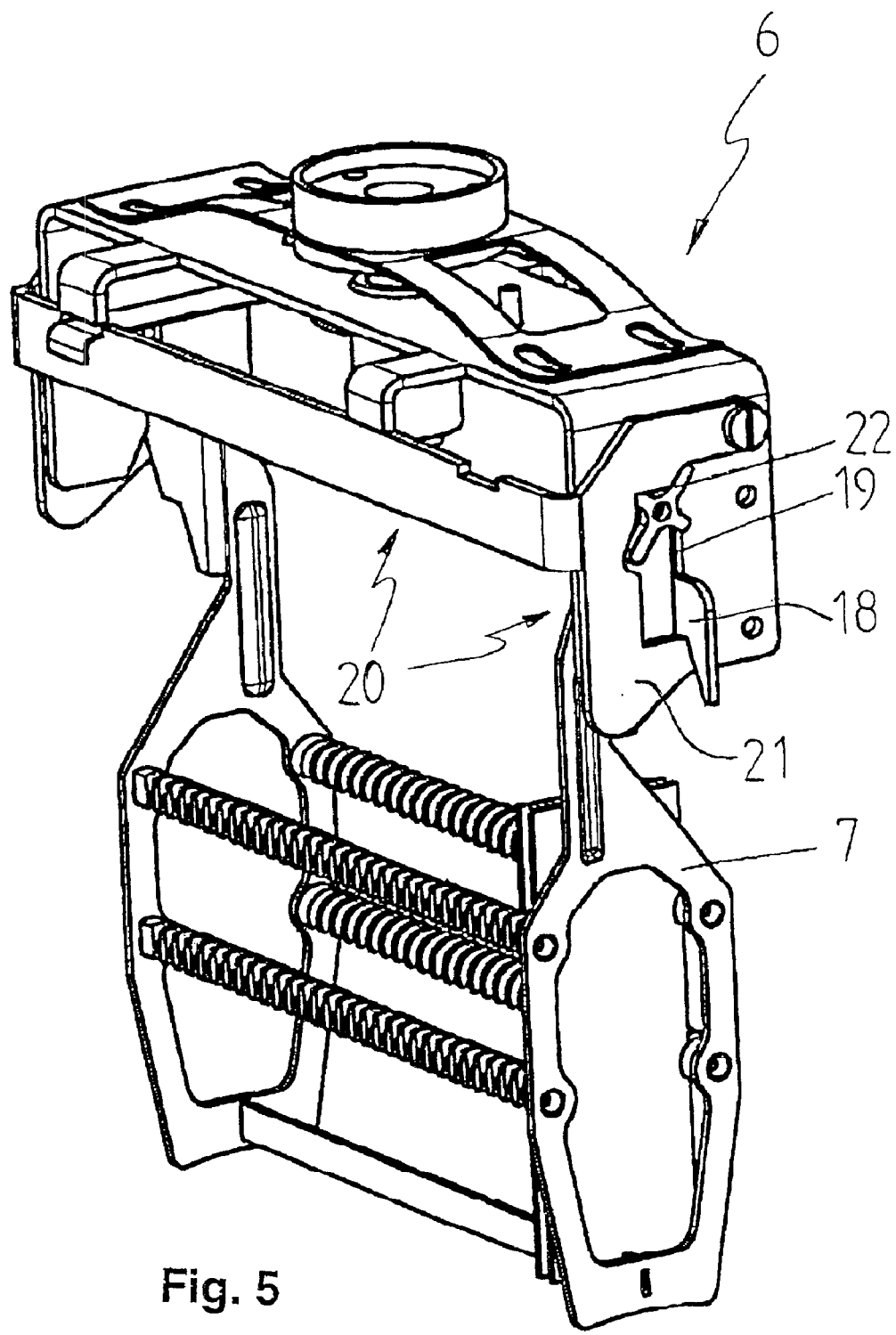
FIG. 5 schematically depicts a second exemplary embodiment.
Figure 6A:
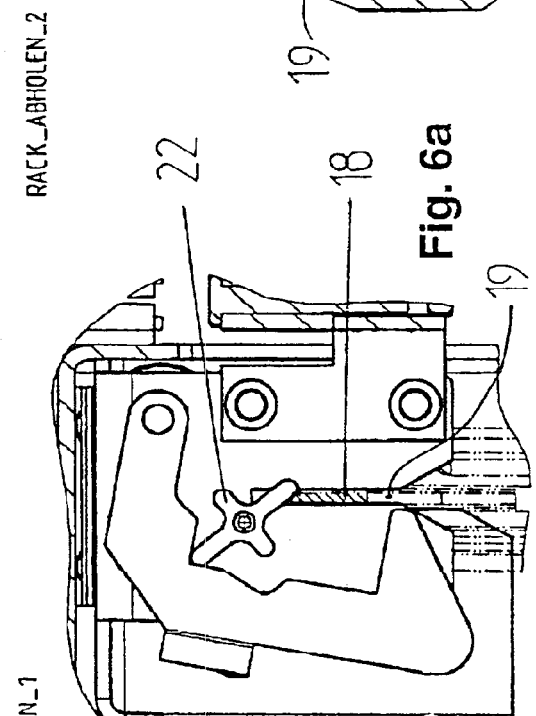
FIGS. 6a–d show, in schematic partial views, the manner of operation of the gripper of FIG. 5.
Figure 6B:
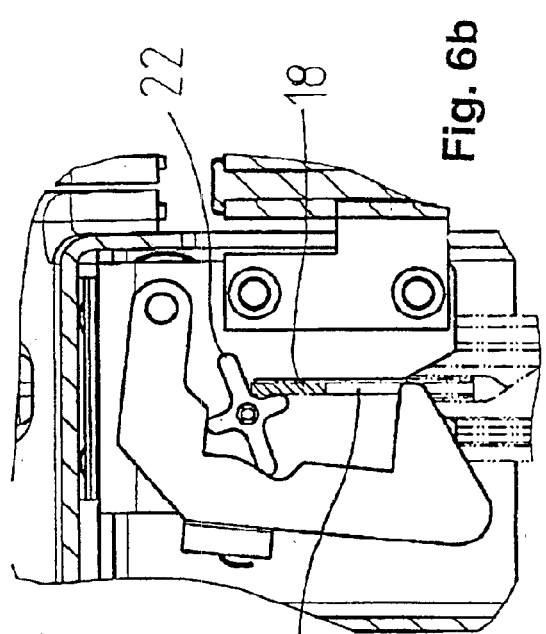
Figure 6C:
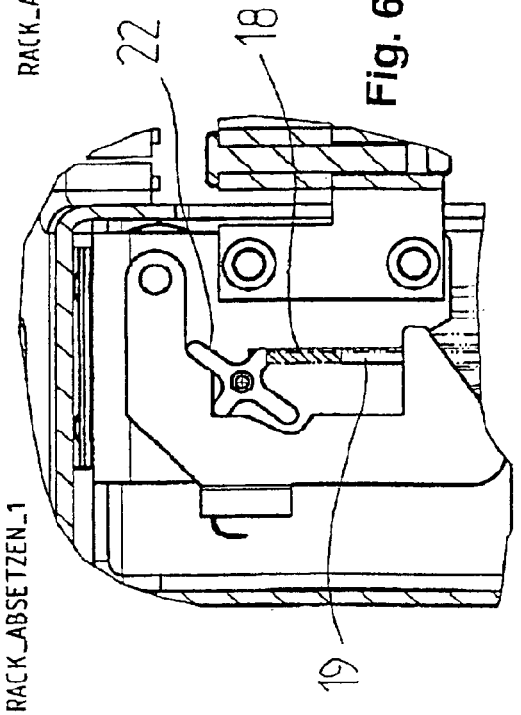
Figure 6D:
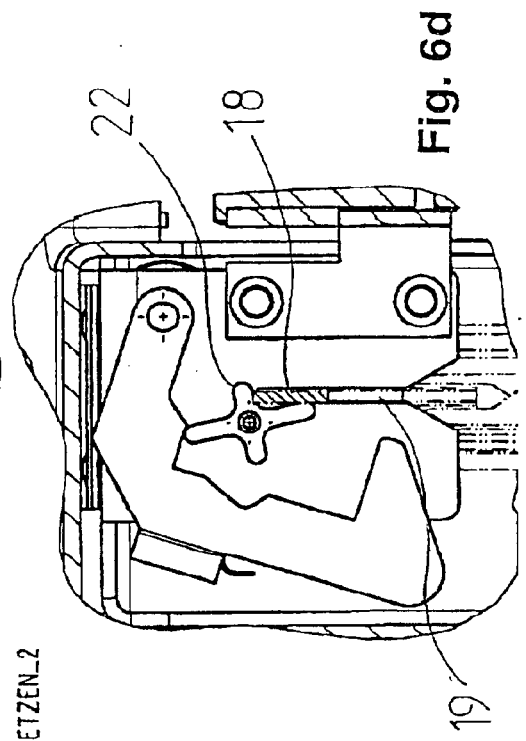

In the case of the exemplary embodiment shown in FIG. 5 it is also possible for gripper 6 to travel onto object holder 7 from directly above; as gripper 6 and object holder 7 interact in this context, slot 19 more or less surrounds hooks 18 of object holder 7, specifically after actuation of a particular closure/holding mechanism 20.

FIGS. 6a through 6d show, in sequence, the manner of operation of closure/holding mechanism 20 of the apparatus shown in FIG. 5. It is very particularly clearly evident from this that an actuation member 21 is actuated by a switching cross 22, which in turn is actuated by hooks 18 of object holder 7 and thus by closure/holding mechanism 20. The interaction of switching cross 22 and hooks 18, and the manner of operation of closure/holding mechanism 20, is evident from the sequence shown in FIGS. 6a through 6d.

Figure 7:
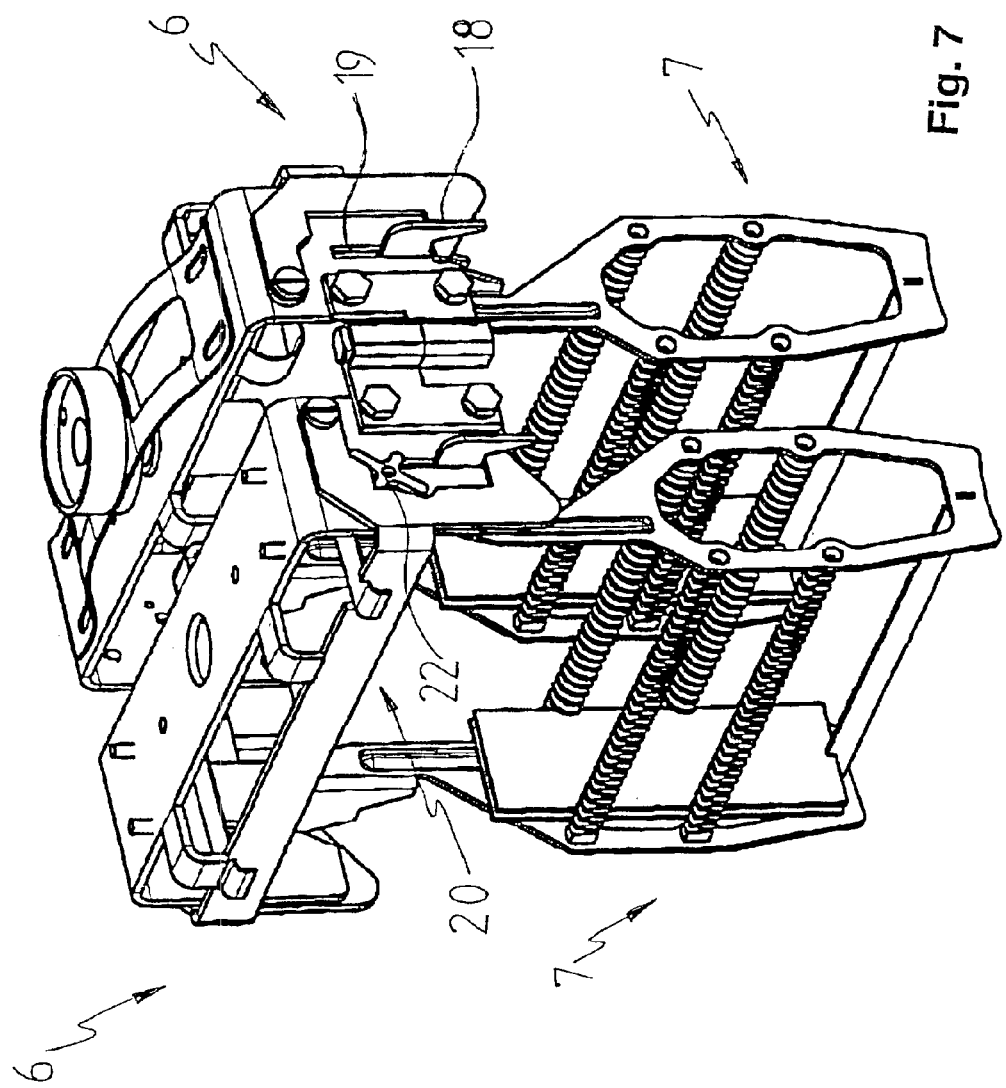
FIG. 7 schematically depicts a double gripper.

FIG. 7 further shows a particular embodiment of gripper 6 at the end of robot arm 5 (not shown therein); namely the provision of two grippers 6 or of a double gripper for concurrent reception of two object holders 7. In the exemplary embodiment shown here, grippers 6 and object holders 7 are immovably coupled to one another and thus can be moved only together. A higher throughput as a result of concurrent movement of two objects or object holder 7 is thus possible, thereby increasing throughput.

In conclusion, be it noted that the exemplary embodiments discussed above serve merely to describe the teaching claimed, but do not limit it to the exemplary embodiments.
Parts List
1 Automatic stainer
2 Processing station, treatment station
3 Vessel
4 Transport device
5 Robot arm
6 Gripper
7 Object holder
8 Linear shaft
9 Drive (for height adjustment)
10 Guide (for linear shaft)
11 Mounting means (for guide on baseplate)
12 Partial arm (associated with linear shaft)
13 Partial arm (carries gripper)
14 Drive belts (in both partial arms)
15 Drive (for drive belts)
16 Drive (for drive belts)
17 Pulleys (to receive and guide drive belts)
18 Hooks (on object holder)
19 Slots (on gripper)
20 Closure/holding mechanism (of gripper)
21 Actuation member (of gripper)
22 Switching cross (of gripper)

What is claimed is:

1. An apparatus for treating cytological or histological specimens comprising:

a plurality of processing stations;

an object holder for carrying at least one specimen, wherein the object holder includes a pair of hooks on opposite sides of the object holder;

a transport device for delivering the object holder into and out of the processing stations, wherein the transport device includes:
a robot arm having a free end movable in three-dimensions;
a gripper mounted at the free end of the robot arm for releasably grasping the object holder, wherein the gripper includes a pair of slots for respectively receiving the pair of hooks of the object holder, each of the pair of slots having a downwardly-facing open end, an actuation member movable to and from a closure position wherein the actuation member closes the open end of each of the pair of slots; and
a rotatable switching cross engaging the actuation member, wherein a rotational position of the switching cross determines whether the actuation member is in the closure position or away from the closure position, and wherein the switching cross is rotated by engagement thereof with the object holder;

wherein the gripper is actuable to grasp the object holder by lowering the free end of the robot arm to cause the gripper to engage the object holder while the object holder resides in one of the processing stations; and wherein the gripper is actuable to release the object holder by lowering the arm end of the robot arm beyond a position at which the object holder resides in and is supported by one of the processing stations.

2. The apparatus according to claim 1, wherein the switching cross is rotated by engagement thereof with one of the pair of hooks of the object holder.

3. The apparatus according to claim 1, wherein the gripper is pivotally mounted at the free end of the robot arm.

* * * * *